United States Patent
Liu

(10) Patent No.: US 9,839,236 B2
(45) Date of Patent: Dec. 12, 2017

(54) ELECTRONIC CIGARETTE CASE AND INFORMATION ACQUISITION METHOD

(71) Applicant: HUIZHOU KIMREE TECHNOLOGY CO., LTD. SHENZHEN BRANCH, Shenzhen, Guangdong (CN)

(72) Inventor: Qiuming Liu, Guangdong (CN)

(73) Assignee: HUIZHOU KIMREE TECHNOLOGY CO., LTD. SHENZHEN BRANCH, Shenzhen, Guangdong (CN)

( * ) Notice: Subject to any disclaimer, the term of this patent is extended or adjusted under 35 U.S.C. 154(b) by 0 days.

(21) Appl. No.: 15/263,194

(22) Filed: Sep. 12, 2016

(65) Prior Publication Data

US 2016/0374390 A1      Dec. 29, 2016

Related U.S. Application Data

(63) Continuation of application No. PCT/CN2014/074637, filed on Apr. 2, 2014.

(30) Foreign Application Priority Data

Mar. 18, 2014   (CN) .......................... 2014 1 0101593

(51) Int. Cl.
  *G08C 19/22*   (2006.01)
  *H04Q 9/00*   (2006.01)
  (Continued)

(52) U.S. Cl.
  CPC .............. *A24F 15/18* (2013.01); *A24F 15/20* (2013.01); *A61L 2/10* (2013.01); *B65D 25/10* (2013.01);
  (Continued)

(58) Field of Classification Search
  CPC ........ A24F 15/18; A24F 15/20; A24F 47/008; B65D 25/10; A61L 2/10; A61L 2202/11;
  (Continued)

(56) References Cited

U.S. PATENT DOCUMENTS

2010/0242974 A1   9/2010  Pan
2011/0181421 A1   7/2011  Nabata
(Continued)

FOREIGN PATENT DOCUMENTS

CN    201094280 Y    8/2008
CN    101518361 A    9/2009
(Continued)

OTHER PUBLICATIONS

International Search Report for PCT/CN2014/074637, dated Dec. 19, 2014, ISA/CN.

*Primary Examiner* — Erin File
(74) *Attorney, Agent, or Firm* — U.S. Fairsky LLP; Yue Xu

(57) ABSTRACT

An electronic cigarette case and an information acquisition method are provided. The electronic cigarette case includes: a case body; a microcontroller arranged inside said case body; a trigger module, used for generating a trigger signal, being arranged on said case body; said trigger module being connected to said microcontroller; said microcontroller being used for acquiring, according to said trigger signal, a user smoking signal from the electronic cigarette; a GPS transmission module connected to said microcontroller and used for transmitting said user smoking information to a preset database.

12 Claims, 2 Drawing Sheets

(51) Int. Cl.
*A24F 15/18* (2006.01)
*A24F 15/20* (2006.01)
*A61L 2/10* (2006.01)
*B65D 25/10* (2006.01)
*A24F 47/00* (2006.01)
*H02J 7/00* (2006.01)

(52) U.S. Cl.
CPC .............. *H04Q 9/00* (2013.01); *A24F 47/008* (2013.01); *A61L 2202/11* (2013.01); *H02J 7/0045* (2013.01); *H02J 7/0047* (2013.01); *H02J 2007/005* (2013.01); *H02J 2007/0096* (2013.01)

(58) Field of Classification Search
CPC .... H04Q 9/00; H02J 7/0047; H02J 2007/005; H02J 2007/0096; H02J 7/0045
See application file for complete search history.

(56) References Cited

U.S. PATENT DOCUMENTS

| | | | | |
|---|---|---|---|---|
| 2013/0284192 | A1* | 10/2013 | Peleg | A24F 47/002 131/329 |
| 2013/0319439 | A1* | 12/2013 | Gorelick | A24F 47/008 131/329 |
| 2013/0342157 | A1 | 12/2013 | Liu | |
| 2014/0107815 | A1* | 4/2014 | LaMothe | A24F 15/18 700/90 |
| 2014/0174459 | A1* | 6/2014 | Burstyn | A24F 47/008 131/273 |
| 2014/0202477 | A1* | 7/2014 | Qi | A24F 47/008 131/329 |
| 2014/0305450 | A1* | 10/2014 | Xiang | A24F 47/008 131/329 |
| 2015/0181945 | A1* | 7/2015 | Tremblay | A24F 47/008 131/328 |
| 2015/0304401 | A1* | 10/2015 | Liu | A24F 47/008 709/217 |
| 2016/0227842 | A1* | 8/2016 | Xiang | A24F 47/008 |
| 2017/0118292 | A1* | 4/2017 | Xiang | H04L 67/12 |

FOREIGN PATENT DOCUMENTS

| | | |
|---|---|---|
| CN | 201374580 Y | 12/2009 |
| CN | 201700404 U | 1/2011 |
| CN | 102188050 A | 9/2011 |
| CN | 102835737 A | 12/2012 |
| CN | 203262287 U | 11/2013 |
| CN | 203326663 U | 12/2013 |
| CN | 203446536 U | 2/2014 |

\* cited by examiner

ELECTRONIC CIGARETTE CASE AND INFORMATION ACQUISITION METHOD

CROSS REFERENCE OF RELATED APPLICATION

This application is a continuation of International Application No. PCT/CN2014/074637, titled "ELECTRONIC CIGARETTE CASE AND INFORMATION ACQUISITION METHOD", filed on Apr. 2, 2014, which claims priority to Chinese Patent Application No. 201410101593.0, entitled "ELECTRONIC CIGARETTE CASE AND INFORMATION ACQUISITION METHOD", filed on Mar. 18, 2014 with the State Intellectual Property Office of People's Republic of China, both of which are incorporated by reference in entirety.

FIELD

The present disclosure relates to the technical field of electronic cigarette, and in particular to an electronic cigarette case and an information acquisition method.

BACKGROUND

As people are becoming increasingly health conscious, it is appreciated by more and more people that smoking is harmfulness. Therefore, electronic cigarettes, which are healthier than cigarettes, are more and more popular.

An electronic cigarette case is provided for receiving an electronic cigarette. At present, the electronic cigarette case is mainly provided for charging the electronic cigarette and receiving the electronic cigarette. Specifically, a microcontroller arranged inside the electronic cigarette case controls a cigarette case battery arranged inside the electronic cigarette case to charge a battery of an electronic cigarette inserted into the electronic cigarette case. Alternatively, the microcontroller controls an external power source to charge the battery of the electronic cigarette inserted into the electronic cigarette case. A charging frequency of the electronic cigarette by a user is related to a usage of the electronic cigarette by the user, and the usage of the electronic cigarette by the user is closely related to the health of the user. Therefore, it is desired to provide a user with an appropriate electronic cigarette by learning a smoking habit of the user without any influence on a normal usage of an existing electronic cigarette by the user.

SUMMARY

Embodiments of the present disclosure provide an electronic cigarette case and an information acquisition method, for acquiring user smoking information.

An electronic cigarette case is provided, which includes a case body; a microcontroller arranged inside the case body; and a trigger module arranged on the case body and configured to generate a trigger signal. The trigger module is connected to the microcontroller, and the microcontroller is configured to acquire user smoking information from an electronic cigarette in response to the trigger signal. The electronic cigarette case further includes a Global Positioning System (GPS) transmitting module connected to the microcontroller. The GPS transmitting module is configured to transmit the user smoking information to a preset database.

In the electronic cigarette case, inside the case body, a cigarette case battery may be arranged and connected to the microcontroller, and an electronic cigarette battery charging interface may be arranged and configured for charging a battery of the electronic cigarette. The trigger module may be configured to generate the trigger signal when the electronic cigarette battery charging interface of the electronic cigarette case is electrically connected to the battery of the electronic cigarette.

In the electronic cigarette case, a slot may be arranged inside the case body for receiving the electronic cigarette, and the electronic cigarette battery charging interface may be arranged in the slot. A sterilization device may be arranged in the slot and connected to the microcontroller. An operation button may be arranged on an outer surface of the case body and configured to enable the microcontroller to control to turn on and turn off the sterilization device.

In the electronic cigarette case, a first detection module may be connected to the microcontroller and configured to detect the charge level of the cigarette case battery, and the microcontroller may generate a first control signal based on the charge level of the cigarette case battery detected by the first detection module. Multiple light-emitting elements may be connected to the microcontroller and configured to indicate the charge level of the cigarette case battery, and the microcontroller may control to turn on and turn off the light-emitting elements by means of the first control signal.

In the electronic cigarette case, a second detected module may be connected to the microcontroller and configured to detect a charge level of the battery of the electronic cigarette in response to the trigger signal, and the microcontroller may generate a second control signal based on the charge level of the battery of the electronic cigarette detected by the second detection module.

Multiple light-emitting elements may be connected to the microcontroller and configured to indicate the charge level of the battery of the electronic cigarette, and the microcontroller may control to turn on and turn off the light-emitting elements by means of the second control signal.

In the electronic cigarette case, the user smoking information may include at least one of a time duration of each puff of a user, a time duration of each time of smoking of the user, a time interval between two adjacent puffs in each time of smoking of the user, the number of puffs of the user every day and a time point of smoking of the user every day.

An information acquisition method is further provided, which includes triggering an electronic cigarette case to generate a trigger signal; acquiring, by the electronic cigarette case, user smoking information in response to the trigger signal; and transmitting, by the electronic cigarette case, the user smoking information to a preset database via a global positioning system.

In the information acquisition method, an electronic cigarette may include a battery, and the electronic cigarette case may include an electronic cigarette battery charging interface.

the electronic cigarette case may generate a trigger signal when the battery of the electronic cigarette is electrically connected to the electronic cigarette battery charging interface of the electronic cigarette case.

In the information acquisition method, the electronic cigarette case may acquire the user smoking information from the electronic cigarette via the electronic cigarette battery charging interface.

In the information acquisition method, the user smoking information may include at least one of a time duration of each puff of a user, a time duration of each time of smoking of the user, a time interval between two adjacent puffs in each time of smoking of the user, the number of puffs of the user every day and a time point of smoking of the user every day.

It can be seen from the above technical solutions that, the embodiments have the following advantages.

In the embodiment, the electronic cigarette case includes the trigger module configured to generate the trigger signal, the microcontroller configured to acquire the user smoking information from the electronic cigarette in response to the trigger signal, and the GPS transmitting module configured to transmit the user smoking information to the preset database. With the electronic cigarette case, a manufacture can acquire the user smoking information worldwide and at any time, to improve the electronic cigarette based on the acquired smoking habits of the user. Therefore, the electronic cigarette conforms to the usage habits of the user, thereby further improving user experience, and being safer to use and better for the smoker's health.

DETAILED DESCRIPTION

The present disclosure provides an electronic cigarette case to facilitate acquisition of user smoking information by a manufacture.

The technical solution in the embodiment of the invention will be described clearly and completely as follows in conjunction with the drawings. It is apparent that the described embodiments are only some rather than all of the embodiments of the present invention. Any other embodiments obtained by those skilled in the art based on the embodiments in the present disclosure without any creative work fall within the scope of protection of the present disclosure.

Figure 1:
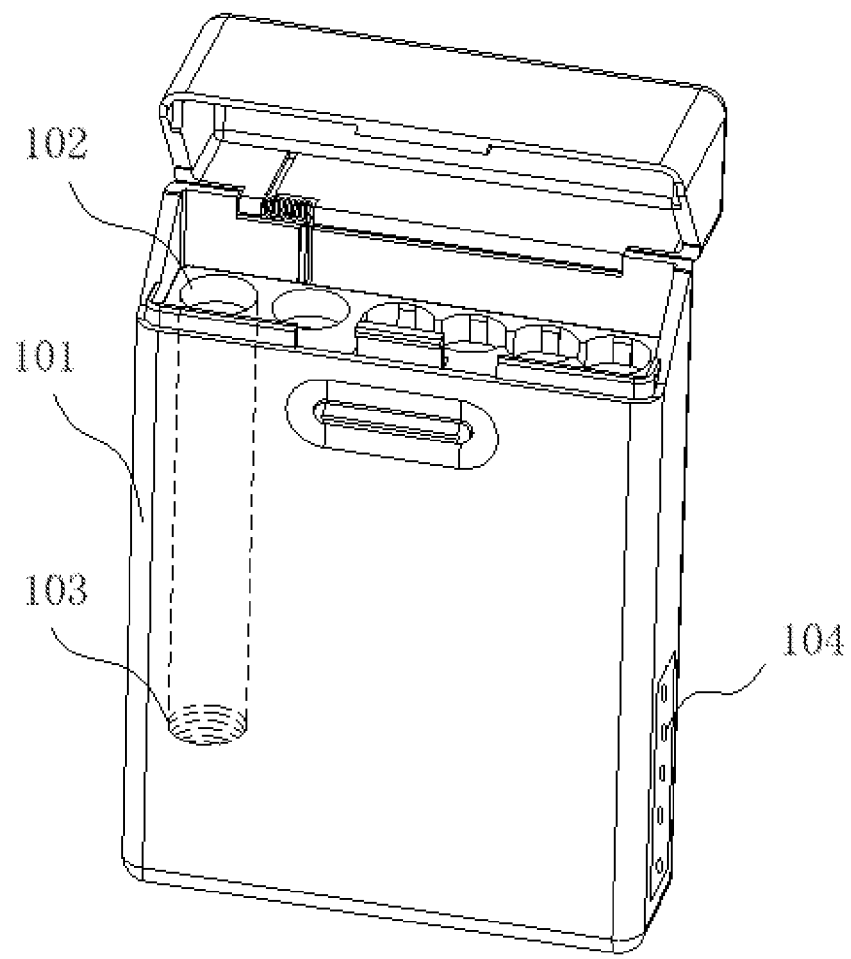
FIG. 1 is a schematic diagram of an overall structure of an electronic cigarette case according to an embodiment.

Reference is made to FIG. 1, which is a schematic diagram of an overall structure of an electronic cigarette case according to an embodiment. As shown in FIG. 1, in an embodiment, the electronic cigarette case includes a case body 101.

The case body 101 is provided for receiving an electronic cigarette. The shape of the case body 101 is preferably a cuboid, a cube or the like, and this is not intended to limiting. On the case body 101, a slot 102 is arranged. The shape of the slot 102 matches the shape of the electronic cigarette, for receiving the electronic cigarette, and this is not intended to limiting. In practice, other structures may be arranged on the case body 101 for receiving the electronic cigarette.

A trigger module (not shown) may be arranged on the case body 101, which is configured to generate a trigger signal. For example, the trigger module may be arranged inside the case body 101 or on an outer surface of the case body 101, and is configured to generate a trigger signal when an electronic cigarette is detected within a preset range of the case body 101. Alternatively, the trigger module may be an inductor arranged on an inner wall of the slot 102, and the inductor is configured to generate a trigger signal when it is detected that an electronic cigarette is inserted into the slot 102. Alternatively, the trigger module may be an elastic switch arranged on an inner wall of the slot 102, and the elastic switch is configured to generate a trigger signal when an electronic cigarette is inserted into the slot 102 and presses the elastic switch. Of course, the above are only for illustrating, but not for limiting.

Figure 2:
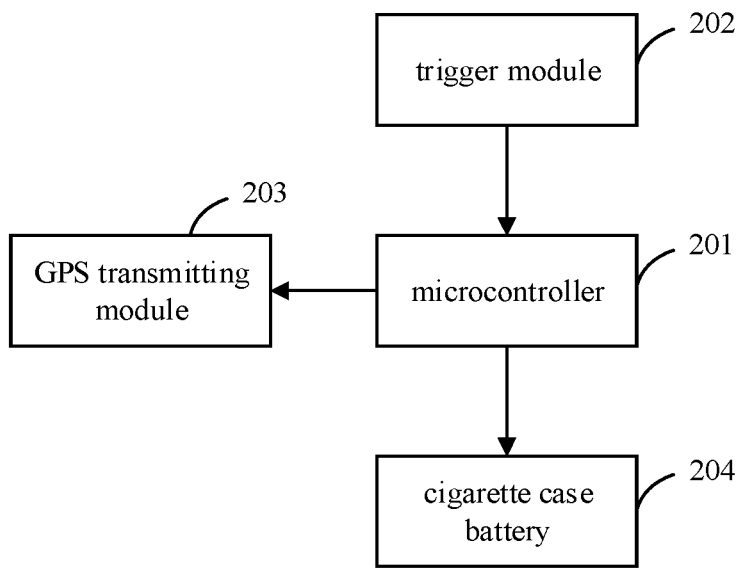
FIG. 2 is a schematic structure diagram of a circuit connection of an electronic cigarette case according to an embodiment.

Reference is made to FIG. 2, which is a schematic structural diagram of a circuit connection of an electronic cigarette case according to an embodiment. Inside the case body 101, a microcontroller 201 is arranged. A trigger module 202 arranged inside the case body 101 is connected to the microcontroller 201. The microcontroller 201 is configured to acquire user smoking information from an electronic cigarette located within a preset range of the case body 101, based on a trigger signal generated by the trigger module 202. The user smoking information is data related to a user smoking an electronic cigarette, such as at least one of a time duration of each puff of a user, a time duration of each time of smoking of the user, a time interval between two adjacent puffs in each time of smoking of the user, the number of puffs of the user every day and a time point of smoking of the user every day. Of course, the above are only for illustrating the smoking information, but not for limiting.

A Global Positioning System (GPS) transmitting module 203 may be further arranged inside the case body 101. The GPS transmitting module 203 is connected to the microcontroller 201, and transmits the user smoking information acquired by the microcontroller 201 to a preset database. The preset database may be built by a manufacture for acquiring information on a user smoking an electronic cigarette.

In the embodiment, the electronic cigarette case includes the trigger module configured to generate the trigger signal, the microcontroller configured to acquire the user smoking information from the electronic cigarette in response to the trigger signal, and the GPS transmitting module configured to transmit the user smoking information to the preset database. With the electronic cigarette case, a manufacture can acquire the user smoking information worldwide and at any time, to improve the electronic cigarette based on the acquired smoke habits of the user. Therefore, the electronic cigarette conforms to usage habits of the user thereby further improving user experience, and being safer to use and better for the smoker's health.

In the embodiment, inside the case body 101, a cigarette case battery 204 (referring to FIG. 2) may be further arranged and connected to the microcontroller 201, and an electronic cigarette battery charging interface 103 (referring to FIG. 1) may be arranged and configured for charging a battery of an electronic cigarette. The electronic cigarette battery charging interface 103 is arranged at the bottom of the slot 102. With this, once the electronic cigarette is placed into the slot 102, the electronic cigarette is electrically connected to the electronic cigarette battery charging interface 103, and the electronic cigarette is charged by the cigarette case battery 204. In practice, in an electronic cigarette case without a slot, the electronic cigarette battery charging interface may be arranged anywhere else, as long as the electronic cigarette battery charging interface can be electrically connected to an electronic cigarette placed in the electronic cigarette case.

Preferably, the trigger module 202 may be a same one component as the electronic cigarette battery charging interface 103 of the electronic cigarette case, and is configured to generate the trigger signal when the electronic cigarette battery charging interface 103 of the electronic cigarette case is electrically connected to the battery of the electronic cigarette. The microcontroller 201 is configured to acquire, in response to the trigger signal, user smoking information from the electronic cigarette which is electrically connected to the electronic cigarette battery charging interface 103, with the user smoking information being stored in the electronic cigarette. Thus, the cost for further arranging a trigger module on the electronic cigarette case is reduced.

Preferably, a sterilization device (not shown) may be further arranged in the slot 102 and connected to the microcontroller 201. An operation button (not shown) may be arranged on an outer surface of the case body 101 and configured to enable the microcontroller 201 to control to turn on and turn off the sterilization device. If a user wants to sterilize an electronic cigarette placed in the electronic cigarette, the user may press the operation button arranged on the outer surface of the case body 101. Then, the microcontroller 201 may turn on the sterilization device in response to the operation of the user, thereby improving the health and safety of the electronic cigarette. Specifically, the sterilization device may be an ultraviolet germicidal lamp. Of course, the above are only for illustrating, but not for limiting. Further, a retroreflective sheeting (not shown) may be further arranged in the slot 102, and the ultraviolet germicidal lamp and the retroreflective sheeting may be arranged in line. With this, the electronic cigarette is sterilized by the turned-on ultraviolet germicidal lamp via the retroreflective sheeting, thereby ensuring the safe usage of the electronic cigarette by the user.

Preferably, at least one elastic soft block (not shown) is further arranged in the slot 102 for gripping the electronic cigarette. In the elastic soft block, a gripping hole is arranged and configured to grip the electronic cigarette. The electronic cigarette is fixed in the electronic cigarette case by placing the electronic cigarette in the gripping hole of the elastic soft block. Further, at least one convex retaining portion is arranged on an inner wall of the gripping hole, and the retaining portion and the electronic cigarette are pressed against each other. With the retaining portion, the electronic cigarette placed in the electronic cigarette case cannot be shaken, and thus the electronic cigarette can be placed in the electronic cigarette case steadily.

Preferably, a first detection module (not shown) may be further connected to the microcontroller 201. The first detection module is configured to detect a charge level of the cigarette case battery 204. Multiple light-emitting elements 104 (referring to FIG. 1) may be further arranged on the outer surface of the electronic cigarette case. In practice, these light-emitting elements 104 may be embedded into a surface of the electronic cigarette case. The light-emitting elements 104 each are connected to the microcontroller 201 to indicate the charge level of the cigarette case battery. Specifically, the microcontroller 201 is configured to generate a first control signal based on the charge level of the cigarette case battery 204 detected by the first detection module, and controls, based on the first control signal, a corresponding number of light-emitting elements to emit lights, to indicate the charge level of an electricity cigarette battery or the charge level of the cigarette case battery.

In practice, the first detection module may be always in operation. Alternatively, an operation button (not shown) may be arranged on the outer surface of the case body 101 for enabling the first detection module. If a user wants to check the charge level of the cigarette case battery 204, the user presses the operation button on the outer surface of the case body 101, and then the first detection module detects the charge level of the cigarette case battery 204 in response to the operation of the user.

Alternatively, instead of the first detection module, a second detection module (not shown) may be connected to the microcontroller 201. The second detection module is configured to detect the charge level of the battery of the electronic cigarette in response to the trigger signal generated by the trigger module. The microcontroller 201 is configured to generate a second control signal based on the charge level of the battery of the electronic cigarette detected by the second detection module, and controls, based on the second control signal, a corresponding number of light-emitting elements 104 to emit lights, to indicate the charge level of the battery of the electronic cigarette.

In practice, the first detection module and the second detection module both may be arranged in the electronic cigarette case and connected to the microcontroller 201. At two different locations on the surface of the electronic cigarette case, multiple light-emitting elements may be provided respectively for indicating the charge level of the cigarette case battery and the charge level of the battery of the electronic cigarette, and this is not intended to limiting.

Figure 3:
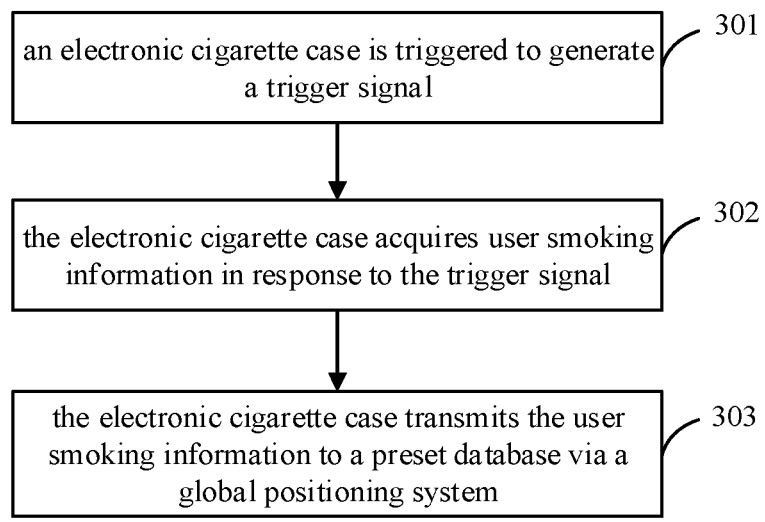
FIG. 3 is a flowchart of an information acquisition method according to an embodiment.

In the above, the electronic cigarette case according to the embodiment has been described. In the following, an information acquisition method according to the embodiment will be described. Referring to FIG. 3, the information acquisition method according to an embodiment includes steps 301 to 303.

In step 301, an electronic cigarette case is triggered to generate a trigger signal.

In the embodiment, the electronic cigarette case is provided for receiving an electronic cigarette. The electronic cigarette case may be configured to be triggered to generate a trigger signal if the electronic cigarette is detected within a preset range of the electronic cigarette case.

Preferably, the electronic cigarette case may be provided with an electronic cigarette battery charging interface, for charging a battery of an electronic cigarette. The electronic cigarette case generates the trigger signal when the battery of the electronic cigarette is electronically connected to the electronic cigarette battery charging interface of the electronic cigarette case.

In practice, the electronic cigarette case may be enabled to generate a trigger signal in other ways, and the above is not intended to limiting.

In step 302, the electronic cigarette case acquires user smoking information in response to the trigger signal.

After the trigger signal is generated, the electronic cigarette case further acquires, in response to the trigger signal, the user smoking information stored in the electronic cigarette. In practice, a recording module may be arranged in the electronic cigarette, for recording information such as a smoking habit of a user. For example, the user smoking information may include at least one of a time duration of each puff of a user, a time duration of each time of smoking of the user, a time interval between two adjacent puffs in each time of smoking of the user, the number of puffs of the user every day and a time point of smoking of the user every day. Of course, the above descriptions are only for illustrating, but not for limiting.

Preferably, in a case that the electronic cigarette case includes the electronic cigarette battery charging interface, when the battery of the electronic cigarette is electrically connected to the electronic cigarette battery charging interface of the electronic cigarette case to enable the electronic cigarette case to generate the trigger signal and acquire the user smoking information in response to the trigger signal, the electronic cigarette case acquires, via the electronic cigarette battery charging interface, the user smoking information from the electronic cigarette electronically connected to the electronic cigarette battery charging interface, with the user smoking information being recorded in the electronic cigarette.

In step 303, the electronic cigarette case transmits the user smoking information to a preset database via a global positioning system (GPS).

In order to acquire user smoking information as much as possible to facilitate an improvement on electronic cigarette based on the user smoking information by a manufacture, the electronic cigarette case, after acquiring the user smoking information, transmits the user smoking information to a preset database. The preset database is generally built by the manufacture for a statistical analysis on the user smoking information of each user.

A GPS transmitting module may be arranged inside the electronic cigarette case, for transmitting the user smoking information to the present database in a wireless manner. The GPS transmitting module and the communication between the GPS transmitting module and a satellite are known in the art, and will not be described hereinafter.

Various embodiments in the specification are described in a progressive way, each embodiment lays emphasis on difference from other embodiments. For the same or similar parts between various embodiments, reference may be made to the description of other embodiments.

The above descriptions of the disclosed embodiments are provided to enable the skilled in the art to practice or use the present disclosure. Various modifications to the embodiments are apparent to the skilled in the art. The general principle suggested herein can be implemented in other embodiments without departing from the spirit or scope of the disclosure. Therefore, the invention would not be limited to the embodiments disclosed herein, but is to be accorded with the widest scope consistent with the principles and the novel features disclosed herein.

The invention claimed is:

1. An electronic cigarette case, comprising:
   a case body;
   a microcontroller arranged inside the case body;
   a trigger module arranged on the case body and configured to generate a trigger signal, wherein the trigger module is connected to the microcontroller, and the microcontroller is configured to acquire user smoking information from an electronic cigarette in response to the trigger signal;
   a Global Positioning System (GPS) transmitting module connected to the microcontroller, wherein the GPS transmitting module is configured to transmit the user smoking information to a preset database; and
   a cigarette case battery arranged inside and connected to the microcontroller, and the cigarette case battery comprising an electronic cigarette battery charging interface arranged to charge a battery of the electronic cigarette;
   wherein the trigger module is configured to generate the trigger signal when the electronic cigarette battery charging interface of the electronic cigarette case is electrically connected to the battery of the electronic cigarette.

2. The electronic cigarette case according to claim 1, wherein
   a slot is arranged inside the case body for receiving the electronic cigarette, and the electronic cigarette battery charging interface is arranged in the slot;
   a sterilization device is arranged in the slot and connected to the microcontroller; and
   an operation button is arranged on an outer surface of the case body and configured to enable the microcontroller to control to turn on and turn off the sterilization device.

3. The electronic cigarette case according to claim 1, wherein
   a first detection module is connected to the microcontroller and configured to detect a charge level of the cigarette case battery, and the microcontroller generates a first control signal based on the charge level of the cigarette case battery detected by the first detection module; and
   a plurality of light-emitting elements are connected to the microcontroller and configured to indicate the charge level of the cigarette case battery, and the microcontroller turns on and turns off the plurality of light-emitting elements by means of the first control signal.

4. The electronic cigarette case according to claim 2, wherein
   a first detection module is connected to the microcontroller and configured to detect a charge level of the cigarette case battery, and the microcontroller generates a first control signal based on the charge level of the cigarette case battery detected by the first detection module; and
   a plurality of light-emitting elements are connected to the microcontroller and configured to indicate the charge level of the cigarette case battery, and the microcontroller turns on and turns off the plurality of light-emitting elements by means of the first control signal.

5. The electronic cigarette case according to claim 1, wherein
   a second detected module is connected to the microcontroller and configured to detect a charge level of the battery of the electronic cigarette in response to the trigger signal, and the microcontroller generates a second control signal based on the charge level of the battery of the electronic cigarette detected by the second detection module; and
   a plurality of light-emitting elements are connected to the microcontroller and configured to indicate the charge level of the battery of the electronic cigarette, and the microcontroller turns on and turns off the plurality of light-emitting elements by means of the second control signal.

6. The electronic cigarette case according to claim 2, wherein
   a second detected module is connected to the microcontroller and configured to detect a charge level of the battery of the electronic cigarette in response to the trigger signal, and the microcontroller generates a second control signal based on the charge level of the battery of the electronic cigarette detected by the second detection module; and
   a plurality of light-emitting elements are connected to the microcontroller and configured to indicate the charge level of the battery of the electronic cigarette, and the microcontroller turns on and turns off the plurality of light-emitting elements by means of the second control signal.

7. The electronic cigarette case according to claim 1, wherein
   the user smoking information comprises at least one of a time duration of each puff of a user, a time duration of each time of smoking of the user, a time interval between two adjacent puffs in each time of smoking of the user, the number of puffs of the user every day and a time point of smoking of the user every day.

8. The electronic cigarette case according to claim 1, wherein
the user smoking information comprises at least one of a time duration of each puff of a user, a time duration of each time of smoking of the user, a time interval between two adjacent puffs in each time of smoking of the user, the number of puffs of the user every day and a time point of smoking of the user every day.

9. The electronic cigarette case according to claim 2, wherein
the user smoking information comprises at least one of a time duration of each puff of a user, a time duration of each time of smoking of the user, a time interval between two adjacent puffs in each time of smoking of the user, the number of puffs of the user every day and a time point of smoking of the user every day.

10. An information acquisition method, comprising:
triggering an electronic cigarette case having an electronic cigarette battery charging interface to generate a trigger signal, when a battery of an electronic cigarette is electrically connected to the electronic cigarette battery charging interface of the electronic cigarette case;
acquiring, by the electronic cigarette case, user smoking information in response to the trigger signal; and
transmitting, by the electronic cigarette case, the user smoking information to a preset database via a global positioning system.

11. The information acquisition method according to claim 10, wherein
the electronic cigarette case acquires the user smoking information from the electronic cigarette via the electronic cigarette battery charging interface.

12. The information acquisition method according to claim 10, wherein
the user smoking information comprises at least one of a time duration of each puff of a user, a time duration of each time of smoking of the user, a time interval between two adjacent puffs in each time of smoking of the user, the number of puffs of the user every day and a time point of smoking of the user every day.

* * * * *